United States Patent [19]

Groeninger

[11] Patent Number: 5,189,902
[45] Date of Patent: Mar. 2, 1993

[54] HUMIDITY SENSOR, AND A MEASUREMENT INSTALLATION INCLUDING A PLURALITY OF SUCH SENSORS

[75] Inventor: Kurd G. Groeninger, Le Col Des Roches/Suisse, Switzerland

[73] Assignee: E. G. & G., Maurepus, France

[21] Appl. No.: 638,838

[22] Filed: Jan. 8, 1991

[30] Foreign Application Priority Data

Jan. 8, 1990 [FR] France .................... 90 00128

[51] Int. Cl.$^5$ ............................................ G01W 1/00
[52] U.S. Cl. .................................. 73/24.06; 73/29.05; 73/336.5
[58] Field of Search ............. 73/336.5, 24.04, 24.06, 73/29.01, 29.05

[56] References Cited

U.S. PATENT DOCUMENTS

| | | | |
|---|---|---|---|
| 3,534,585 | 10/1970 | Webb | 73/24.04 |
| 4,561,286 | 12/1985 | Sekler et al. | 73/24.06 |

FOREIGN PATENT DOCUMENTS

| | | | |
|---|---|---|---|
| 0072744 | 2/1983 | European Pat. Off. | |
| 86447 | 5/1983 | Japan | 73/29.05 |
| 932390 | 5/1982 | U.S.S.R. | 73/29.05 |
| 2178539 | 2/1987 | United Kingdom | 73/29.05 |

OTHER PUBLICATIONS

Sensors and Actuators, vol. 11, No. 4, mai/juin 1987, pp. 319–328, Lausanne, CH; J. P. Randin et al.: "Relative humidity measurements using a coated piezoelectric quartz crystal sensor".

Advances in Instrumentation, vol. 41, part 1, 1986, pp. 301–307, Research Triangle Park, NC, US; W. P. Carey et al.: "The IBM-XT and sensor arrays for environmental monitoring".

*Primary Examiner*—Hezron E. Williams
*Assistant Examiner*—Joseph W. Roskos

[57] ABSTRACT

A relative humidity or water activity sensor includes a body defining a cavity with at least one resonant humidity sensing element comprising a crystal plate coated in part with an adsorbent material and at least one resonant temperature sensing element disposed inside the cavity. A membrane suitable for passing water vapor acts as a barrier to liquids and is situated between the cavity and the medium whose relative humidity and/or water activity is to be measured. The value of the relative humidity or of the water activity of the medium, and the temperature are determined from the resonant frequencies of the sensing elements. The invention also provides an installation including a plurality of such sensors.

14 Claims, 4 Drawing Sheets

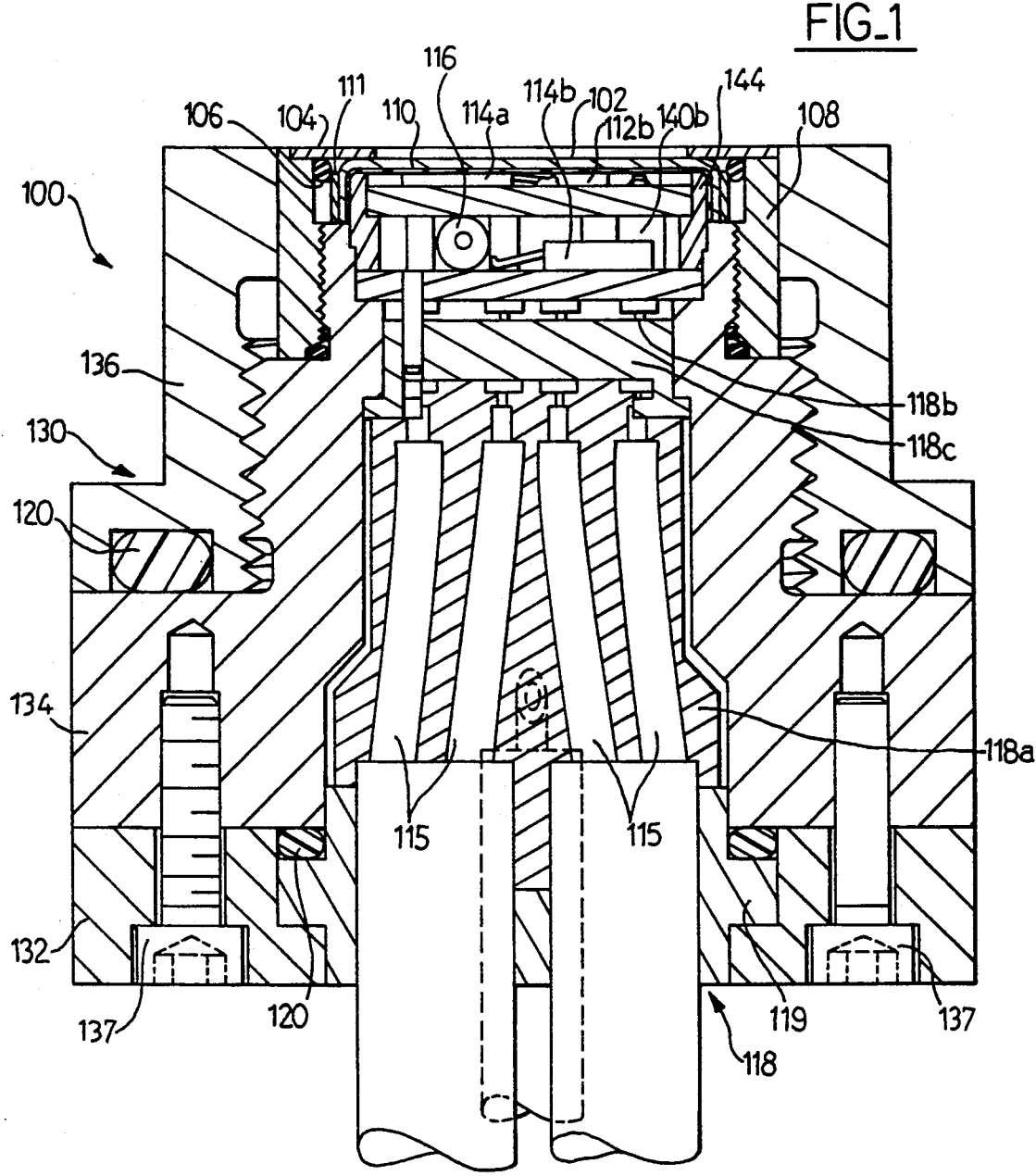
FIG_1
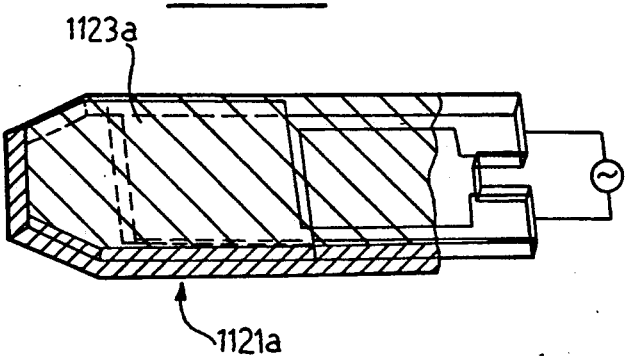
FIG_3

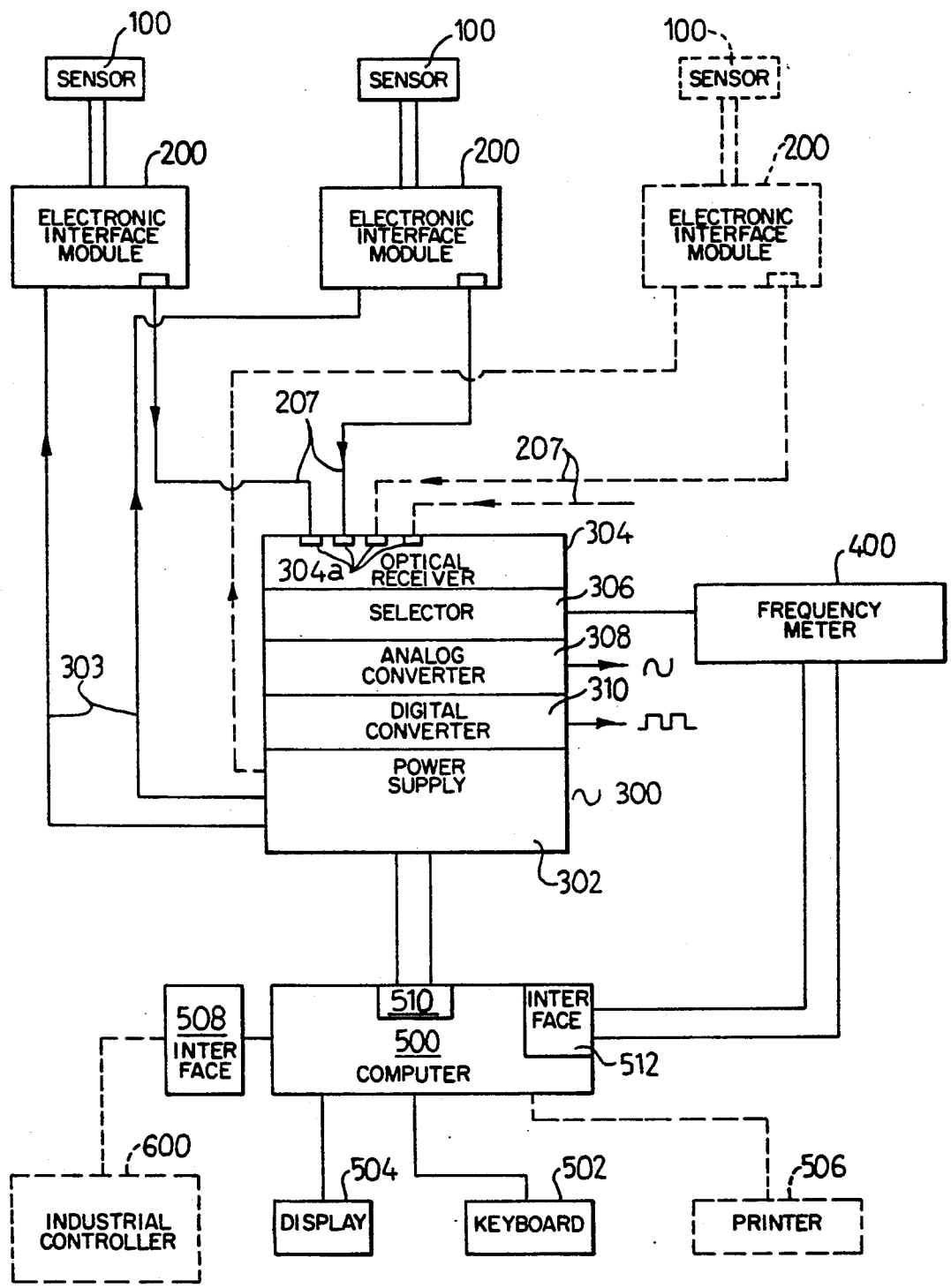
FIG_4

HUMIDITY SENSOR, AND A MEASUREMENT INSTALLATION INCLUDING A PLURALITY OF SUCH SENSORS

The present invention relates in general to a sensor for sensing relative humidity or water activity, and to an installation including such sensors.

BACKGROUND OF THE INVENTION

In the prior art, relative humidity or water activity has been measured in an industrial medium, e.g. powder or granular products flowing along ducts, by putting an adsorbant or a desorbant material in contact with the atmosphere in said substance and by measuring variations in electrical parameters that result from variations in the quantity of water adsorbed or desorbed by the substance. More precisely, it is now known how to make relative humidity measurements by determining variations in electrical resistance or variations in the dielectric constant of such a material as a function of the quantity of water it contains.

A major drawback of known solutions lies in that they all require a current or a voltage to be established, with variations in the amplitude thereof providing the looked-for relative humidity information after being processed. It is therefore necessary to make use of very high quality electronic apparatuses in order to avoid any inaccuracy resulting from variations in the amplitude of the electrical quantity that are not due to variations in the quantity of water. In practice, measuring devices of affordable cost do not provide high accuracy.

The present invention seeks to mitigate these drawbacks of the prior art and to propose a novel sensor and a novel installation enabling relative humidity and/or water activity in an atmosphere, and where applicable water content in a solid medium, to be measured extremely accurately.

SUMMARY OF THE INVENTION

To this end, a first aspect of the present invention provides a relative humidity or water activity sensor comprising, in combination:

a body defining a cavity;

at least one resonant humidity sensing element comprising a crystal plate coated at least in part with an adsorbant material and disposed inside the cavity;

at least one resonant temperature sensing element also disposed inside the cavity;

at least one membrane suitable for passing water vapor while constituting a barrier to liquids, the membrane being situated between the cavity and the medium whose relative humidity and/or water activity is to be measured; and means for determining the resonant frequencies of the sensing elements and for deducing the value of the relative humidity of the water activity of the medium, and also for deducing temperature.

Preferred, but non-limiting features of the sensor of the invention are as follows:

each humidity sensing element is housed in an open ceramics package;

it includes two identical humidity sensing elements disposed at substantially equal distances from the membrane;

the, or each, temperature sensing element is a quartz crystal resonator and means are provided for determining the resonant frequency of the crystal resonators and for deducing the temperature value therefrom;

two temperature sensing elements are provided, one of which is situated at substantially the same distance from the membrane as the humidity sensing element(s) and the other of which is situated further from the membrane, and temperature regulation means are provided including heater means disposed inside the cavity and controlled as a function of the difference between the temperatures measured by the two temperature sensing elements;

it includes a first printed circuit carrying both humidity sensing elements and the first temperature sensing element, and a second printed circuit carrying the second temperature sensing element and the heater means, the first printed circuit being disposed between the second printed circuit and the membranes.

it further includes a removable connector whose connection elements fixed to the sensor also constitute means for assembling the two printed circuits one above the other;

a stainless steel first membrane is provided in which a plurality of small-sized holes are formed, and an expanded polytetrafluoroethylene second membrane is provided, with the two membranes being placed substantially one against the other and with the stainless steel membrane being situated on the outside relative to the cavity;

the two membranes are mounted on a support ring, itself removably mounted on the body of the sensor; and the thickness of the steel membrane lies in the range 0.02 mm to 0.05 mm, the diameter of the holes lies in the range 0.02 mm to 0.08 mm, and the area of the holes represents about 15% to 25% of the total area of the membrane.

In a second aspect, the present invention provides an installation for measuring water activity and water content of one or more substances in various locations of industrial processing equipment, the installation comprising:

a plurality of sensors as detailed above;

optical modulator means associated with each sensor for delivering an optical signal representative of the electrical resonance signal of the humidity sensing element(s) of the associated sensor; and a central unit connected to the optical modulator means by a plurality of optical fibers and itself comprising:

a plurality of optical demodulators each associated with a respective one of the sensors and suitable for converting received optical signals into electrical signals;

selector means for applying a selected one of said electrical signals on an output;

frequency measurement means; and means for controlling the selector means and for converting frequency values into relative humidity or water activity values for each of the sensors.

Preferred, but non-limiting features of the installation of the present invention are as follows:

when each sensor includes at least two quartz crystal sensing elements, the optical modulator means further include selector means for modulating a selected one of the electrical resonance signals of the various sensing elements;

when each sensor includes at least one humidity sensing element and at least one temperature sensing element, the selection and control means further include means for calculating water content values for the substance(s) on the basis of the water activity values and the temperature values obtained and on the basis of stored water activity/water content isotherm curves associated with the substance(s) whose water activity is being measured;

it further includes display means for displaying changes in water activity and/or water content of the substance(s) as a function of time; and it further includes means for comparing the water activity or water content values with at least one threshold value and for indicating when the threshold(s) is/are exceeded.

BRIEF DESCRIPTION OF THE DRAWINGS

An embodiment of the invention is described by way of example with reference to the accompanying drawings, in which:

FIG. 1 is an overall axial section through a sensor of the present invention;

FIG. 3 is a perspective view in partial section of a sensing element of the sensor of FIGS. 1 and 2;

FIG. 4 is a block diagram of a measurement installation incorporating a plurality of sensors as shown in FIGS. 1 and 2.

We begin by specifying that from one figure to another, items or portions that are identical or similar are designated therein by the same reference numerals.

DETAILED DESCRIPTION

Figure 2:
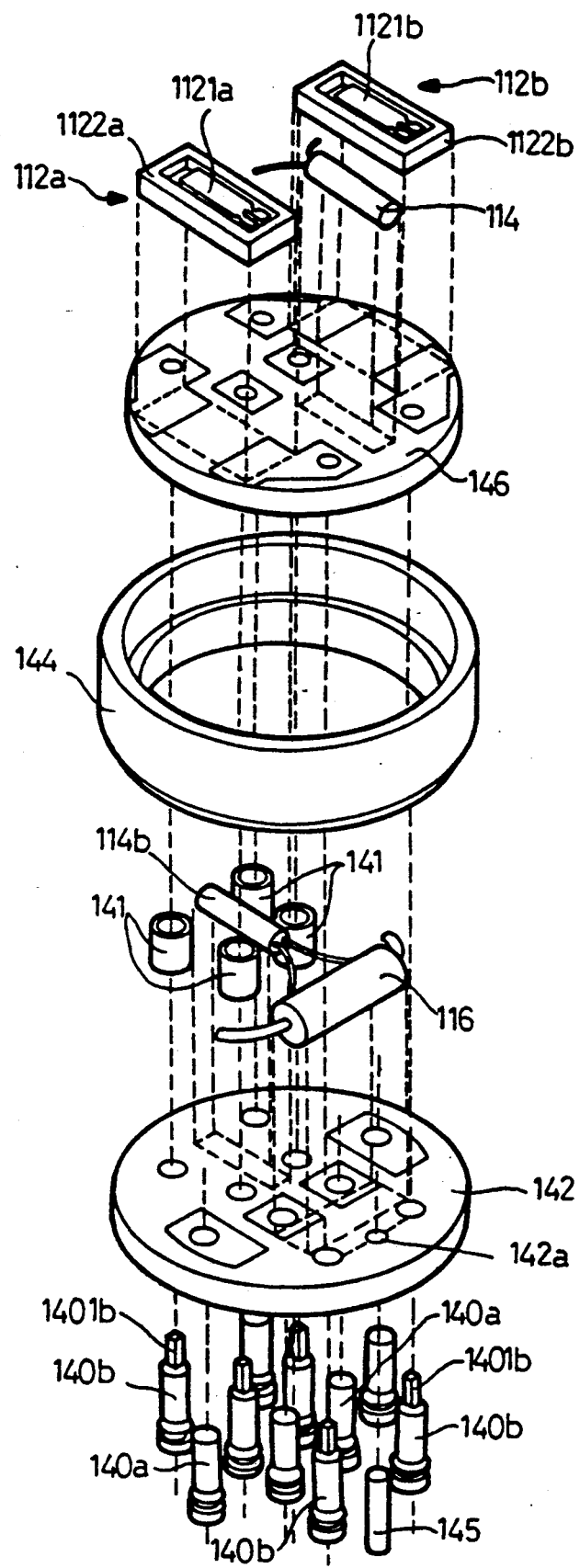
FIG. 2 is an exploded perspective detail view of the FIG. 1 sensor.

With reference initially to FIG. 1, a humidity sensor 100 of the invention comprises a thin membrane 102 which is made of stainless steel in the present example, and in which a plurality of through holes (not visible) are formed. For example, a membrane may be provided which is about 0.03 mm thick, having holes of a diameter of about 0.03 mm to about 0.05 mm, and having about 20% of the surface area of the membrane occupied by the holes.

It should be noted that the membrane 102 could also be made of a ceramic, glass, or the like.

Such a membrane is permeable to gas, but it allows substantially no liquid or solid to pass therethrough, even when the solid is in the form of a fine powder.

The edges of the membrane 102 are held captive between a flat washer 104, likewise made of stainless steel, and a sealing ring 106 made of a resilient material such as rubber, with the assembly being fixed over a front opening of a support ring 108.

The membrane 102 is lined on the inside with a flexible membrane 110 suitable for allowing gas to pass, and in particular water in its vapor form, while preventing the passage of water in its liquid form. It is preferable to select a membrane made of expanded polytetrafluoroethylene known under the trade name "Gore-Tex". It is preferable to choose a membrane having pores with a diameter close to 0.4 μm.

Two identical crystal sensing elements 112a and 112b constituting humidity sensors are to be found behind the membranes 102 and 110 and in the immediate vicinity thereof. A first temperature sensing crystal 114a is provided in the vicinity of the crystals 112a and 112b for measuring the temperature of the environment of said crystals 112a and 112b, together with an electrical power resistance 116a for regulating the temperature in said environment, as explained below.

A second temperature sensing crystal 114b is situated further along the sensor housing, for purposes explained below.

The sensor also includes a rear connector, given overall reference 118, and enabling it to be removably connected to its environment, as explained below.

The inside space of the sensor is sealed by means of O-rings 120 between the various components of the sensor.

The sensor housing which houses the above items is given an overall reference 130 and comprises a body 134 which is screwed into a cover-forming ring 136. The ring may be welded, for example, to the outside surface of a duct conveying a substance whose relative humidity or water activity is to be measured, or else it may be fixed to the end of a stick or rod (not shown) so as to enable it to be inserted into a medium whose relative humidity or water activity is to be measured.

The housing 130 of the sensor also includes a backplate 132. Bolts 137 serve to fix the plate 132 to the body 134.

The connector 118 which is preferably made in the form of an integrally molded body 118a is held prisoner in a cavity defined by the body 134 and the supporting backplate 132 by means of an intermediate ring 119 between said body and plate. The body of the connector 118a houses coaxial conductors 115 whose ends are soldered to male connection pins 118b fixed to a front plate 118c of the connector and suitable for being engaged in associated sockets which are described below.

A first circular printed circuit 142 is received by its edges between a step in the body 134 of the sensor and an annular support member 144. The support member 144 also has a step on which it receives a second circular printed circuit 146 which is situated between the first printed circuit 142 and the membranes 102 and 110.

The second printed circuit 146 carries the two humidity sensing crystals 112a and 112b together with the first temperature sensing crystal 114a, which are mounted by being soldered in place, for example, while the first printed circuit 142 which is situated behind the circuit 146 relative to the membranes 102 and 110, carries the second temperature sensing crystal 114b and the heater resistance 116, which may likewise be held in place by soldering.

As can clearly be seen in FIG. 2, the humidity sensing detecting crystals 112a and 112b are in the conventional form of resonant plates or slabs 1121a and 1121b respectively, and they are housed in respective packages 1122a and 1122b which are preferably made of ceramics. The two connection terminals for each crystal plate (not shown) are provided on the bottom faces of the corresponding packages close to the two ends thereof.

In addition, the various crystals and the resistance are connected to the connection pins 118b of the connector 118 via contact elements 140 each including a female socket at its bottom end for receiving the associated pin. Some of the contact elements 140a are electrically connected only to the bottom printed circuit 142 while nevertheless constituting spacers between the two circuits, while other contact elements 140b include respective extensions 1401b which pass through the top printed circuit and which come into contact with suitable track thereon for soldering thereto.

Insulating sleeves 141 are to be found between the two printed circuits 142 and 146 in order to prevent any accidental electrical contact between the contact elements 140b and their environment, and in particular the temperature sensing element 114b.

In addition, a key 145 co-operates with a same diameter hole 142a formed in the printed circuit 142 to ensure that this circuit takes up the appropriate angle inside the sensor.

The above-mentioned support ring 108 constitutes a lid for the sensor. It is constituted by a component which is essentially annular with internal tapping suitable for being screwed onto a thread 134a on the sensor body 134.

The end of the lid 108 carries the washer 104, the membrane 102, and the O-ring 106, and between itself and the body 134, it imprisons the "Gore-Tex" membrane 110 together with an aluminum ring 111 whose function is to press the edges of said membrane 110 against the outside surface of the printed circuit support 144 for sealing purposes.

In the above-described sensor, all of the items that may come into contact with the substance whose relative humidity or water activity is to be measured (i.e. the washer 104 and the first membrane 102) are made of stainless steel or the like, thereby providing excellent longevity for the sensor. In addition, by having a lid 108 which can be screwed into place, it is easy to replace the membranes, should that be necessary.

FIG. 3 is a diagram showing one of the two identical crystal plates or slabs 1121a constituting the humidity sensing elements.

Sensitivity to humidity is obtained by coating the plate with a material having special properties, in particular with respect to water adsorption. This coating is referenced 1123a in FIG. 3. It is variations in the mass of the plate and its coating as a function of relative humidity Hr or of water activity aW in the medium containing the detector which cause the resonant frequency of the crystal to vary, thereby making it possible to detect variations in the relative humidity or in water activity. Although known per se, it has not been possible in the past to use this principle effectively for measuring water activity on a continuous basis in an industrial process. This principle is described in the article "Piezoelectric Sorption Detector" by William H. King, Jr., published in Analytical Chemistry, Vol. 36, No. 9, August 1964, at pages 1735 et seq, and also in the article "Relative Humidity Measurements Using a Coated Piezoelectric Quartz Crystal Sensor", by Jean-Paul Randin and Freddy Zullig, in the journal: Sensors and Actuators, No. 11, 1987, pp. 319 to 328.

For further details, reference may be made to these two articles, and their respective contents are included in the present description by reference.

The coating material for the quartz plate is selected to obtain as accurate as possible a measurement of relative humidity or of water activity as a function of the following considerations:

it must be hydrophilic and adsorb and desorb water in reproducible manner;

it must have as large as possible a sorption isotherm (quantity of water fixed as a function of ambient relative humidity);

adsorption must take place with a high diffusion coefficient so as to encourage rapid penetration of water molecules;

the sorption isotherms for different temperatures should be as close as possible to one another (a small temperature parameter);

the adsorption/desorption isotherm should have as little hysteresis as possible;

the material must adsorb water extremely selectively compared with other gases;

it must continue to be usable, and with the same isotherms, even after being saturated with water;

it must withstand chemical attach from the gases contained in its atmosphere and it must retain its integrity; and it must be suitable for being made to adhere to the crystal plate easily and reliably, even in a thin layer, and for penetrating into the pores of the crystal while being deposited.

In general, a very wide variety of materials are capable of satisfying the above requirements, and in particular semiconductors, metals and metal oxides, and polymers, especially polymers having a pyridine group.

More particularly, but not exclusively, use is made in the present example of a coating material selected from the group constituted by polysulfone acids, silicon oxide $SiO_x$, modified epoxy resin, and cellulose acetate.

With polymers, the coating can be made by immersing the crystal in a solution containing the coating substance dissolved in a suitable solvent, and then drying. Silicon oxide can be deposited by evaporation.

Naturally, any other technique may be used for making the coating, and in particular vacuum evacuation, cathode sputtering, electroplating, etc. . . . , with the chosen technique depending on the nature of the material.

For further details on such coating materials, reference may be made more particularly to the second-mentioned article by Randin et al.

Further, it may be observed that the crystal plate may be coated with adsorbant material either on both faces, or on one face only, or indeed on a portion only of one or both faces.

The thickness of the coating of adsorbant material preferably lies between a fraction of a micron and a few microns, e.g. it may be around 1 micron.

The temperature sensors are constituted in conventional manner by resonant quartz crystals oscillating at frequencies of about 260 kHz and having the property of reacting very quickly and very accurately to changes in temperature.

The above-described humidity sensor operates as follows. Air (or any other gas or mixture of gases) containing water vapor and flowing along a duct to which the sensor is connected penetrates into the cavity defined in the sensor via the membranes 102 and 110. A quantity of water which is a function of the relative humidity or of the water activity of the gas is adsorbed by the coating on each humidity sensing crystal 112a and 112b, thereby increasing the mass of the resonant slab and causing its resonant frequency to vary. It may be observed that by using two identical humidity crystals and by comparing the frequency variations they give rise to, it is possible to verify that each of them is in good condition.

In addition, the resonant frequency of the temperature sensing crystals 114a and 114b varies as a function of temperature. The frequencies of these two crystals are regularly compared, and in the event of an abnormal temperature difference, the heater resistance 116 is powered to heat the atmosphere situated in the vicinity of the second crystal 114b, thereby balancing the temperature within the cavity of the sensor. This serves to minimize temperature gradients which could have an effect on measurement accuracy.

Variations in the frequency of the resonant slabs of the humidity sensing crystals make it easy to determine the corresponding variations in mass. Given the surface area and the thickness of the adsorbant coating and given its adsorption/desorption characteristic as a function of surrounding relative humidity at a given temperature, it is easy to deduce the relative humidity or water activity in the environment of the slab at a given instant from its mass. Assuming that the gas is in the same state both inside the cavity of the sensor and in the duct (which can be achieved by a suitable choice of membranes), it is then possible to determine the relative humidity or the water activity of the air or other gas in said duct. If, in addition, the water content/water activity isotherms of the substance flowing along the duct are also known, it is finally possible to determine the water content of the substance.

It should be observed that the above operations can be performed in relatively short time, and that the invention makes it possible to track said water content practically in real time.

FIG. 4 shows an installation for measuring relative humidity or water activity and water content by using sensors as described above, and intended to be installed on an industrial site for continuously measuring the water activity of a substance being treated.

In association with each sensor 100 as described above, this installation also includes an electronic interface module 200. The installation also includes a central unit 300, a frequency meter 400, and a computer 500.

Figure 5:
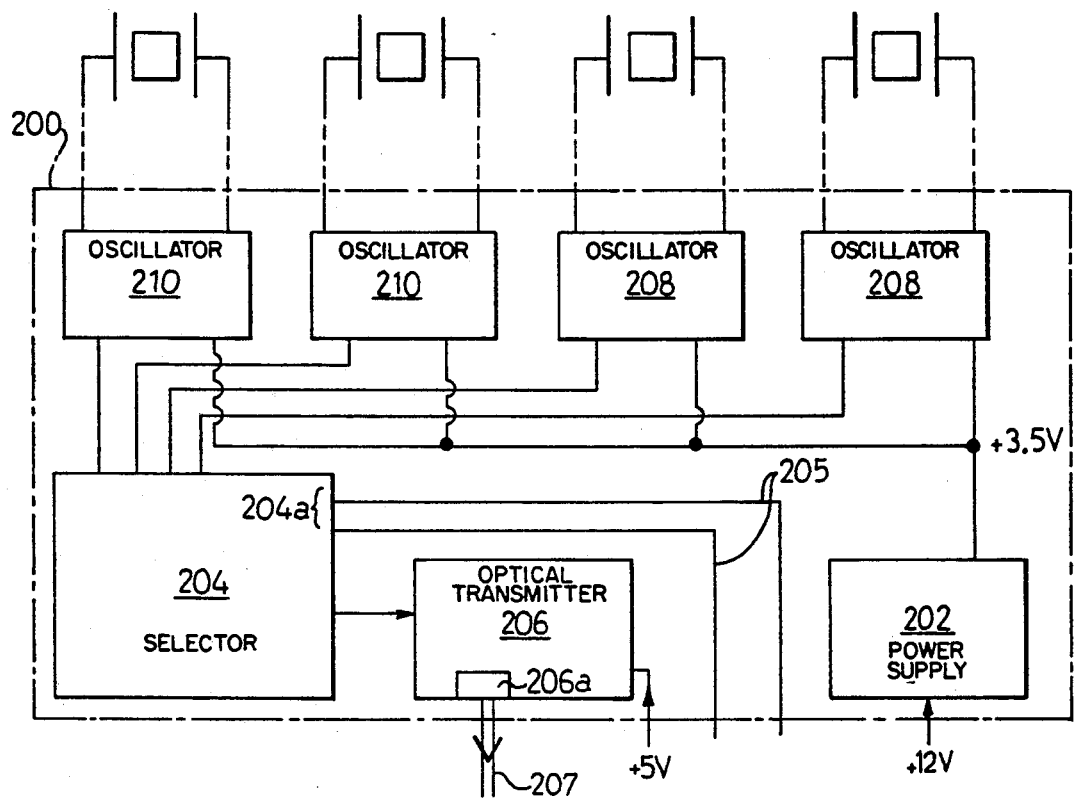
FIG. 5 is a block diagram of a portion of the FIG. 4 installation.

Each module 200 is connected to the associated sensor 100 by the above-described coaxial electric cables 115, with the length of these cables being preferably relatively short, e.g. about 1 meter (m). One such module 200 is shown in detail in FIG. 5.

Each module 200 comprises:

a power supply 202 connected to receive +12 volts from the central unit 300 and to deliver a lower stabilized voltage, e.g. +3.5 volts;

a selector (multiplexer) 204 controlled by the computer 500 via the central unit 300 so as to select one of the four alternating output signals from the crystals 112a, 112b, 114a, and 114b, with inputs for the two binary lines 205 required to select one out of four being referenced 204a;

an optical transmitter 206 whose electrical signal input is connected to the output from the selector 204 and whose optical signal output (generated by a suitable light emitting diode) is suitable for application to an optical fiber 207 via an appropriate connector 206a;

two first oscillators 208 powered by the power supply 202 and associated with respective ones of the water activity measurement crystals 112a and 112b, a frequency of about 10 MHz, for example; and two second oscillators 210 also powered by the power supply 202, associated with the temperature measurement crystals 114a and 114b, and operating at a frequency of about 260 kHz, for example.

Under control of the central unit 300, each module 200 is thus capable of applying an optical signal at any given instant to the optical fiber 207 corresponding to the resonant electrical signal from a selected one of the four measurement crystals. It should be observed that by using a semiconductor selector, it is possible to send these various signals to the central unit at a high switching rate, if necessary.

Each module 200 is thus connected to the associated sensor by eight coaxial cables (e.g. 75 ohm cables) as described above, together with two conductors 212 for feeding the heater resistance 116. In addition, each module 200 is connected to the central unit 300, not only by the optical fiber conveying the output signals from the sensor, but also by a cable containing a plurality of conductors to convey:

the +12 V required by the power supply 202;

the +5 V required to power the optical transmitter;

the +5 V required to power the heater resistance 116;

the two binary selection signals applied to the selector; and ground.

The oscillators are preferably Pierce oscillators based on NAND gate TTL integrated circuits.

In the present example, the central unit 300 is suitable for controlling a set of four sensor 100 and electronic module 200 pairs.

It comprises an electrical power supply 302 suitable for delivering the stablized DC voltages required to operate the various components of the installation, and in particular the +5 V and the +12 V for feeding to the modules 200 via the lines represented by reference 303. There is also a card given overall reference 304 including four optical receivers and four connectors for four optical fibers such as 207 coming from the modules 200, with the card being suitable for converting the received optical signals into electrical signals. It is preferable to use broadband receivers so as to be capable of receiving the frequencies associated with measuring water activity and the frequencies associated with measuring temperature equally well.

By using optical fibers 207, it is possible to have a very great distance between the central unit 300 and the modules 200, e.g. one or more kilometers, thereby enabling the installation to be installed on very large industrial sites.

There is also a multiplexing or selection card 306 which receives the four electrical signals output by the receiver card 304. One particular signal out of these four signals is selected by applying two binary selection signals from the computer 500. The output from the selector 306 is applied to the input of the frequency meter 400 in a manner described in greater detail below. A card 308 may advantageously be provided for delivering water activity, water content, and temperature information in analog form. More precisely, it may be constituted by a card comprising digital-to-analog converters which receive the water activity, water content, and temperature information in digital form from the computer 500 and which convert this information into analog currents or voltages to occupy the ranges commonly used by analog measurement instruments.

An extension card 310 may also be provided for delivering the same signals but in digital form and in TTL format.

The optional cards 308 and 310 provide for extremely flexible connection of the installation constituted by the sensors 100, the electronic modules 200 and the central unit 300 to all kinds of process control equipment or the like.

The frequency meter 400 is preferably a digital frequency meter of conventional design and of high quality. (A temperature compensated or thermostated time base.)

The computer 500 may be a commercially available microcomputer, e.g. a PC clone. It includes a keyboard 502, a display screen 504, e.g. a high definition color screen, a printer 506, and if necessary an interface 508 for communication with a regulating or industrial process controlling computer of any type whatsoever, represented diagrammatically at 600. It also includes two interfaces 510 and 512 for connection with the central unit and with the frequency meter, respectively.

A certain number of possibilities offered by the above-described installation are described briefly below, with most functionality being ensured by suitable programming of the computer 500.

For example, a main program may display a menu to the user, thereby providing access to five subprograms described below.

The main program advantageously also serves to modify various communications parameters, and in particular the serial transmission speed between the computer 500 and the industrial computer 600.

A first subprogram serves to configure the installation, and in particular:

to fix reference values and minimum values and maximum values for the measurements, which values delimit common utilization ranges, and also to fix threshold values which, when exceeded by the measured values, trigger alarms that may be in the form of messages on the screen or in the form of visible or audible warning signals;

to assign an identifier to each sensor, e.g. a name, which identifier appears in screen displays and in printouts;

to indicate the presence of external display screens (other than the screen 504) or of analog outputs;

to fix the time scale for the displayed graphics (and in particular graphics that track measured relative humidity or water activity as a function of time);

to load the computer's volatile memory or mass memory either with sorption isotherms, or else with the addresses of memory locations where such curves are stored, and to modify previously stored isotherms, which isotherms are essential for deducing a water content value from the corresponding water activity and temperature measurements provided by a sensor;

to perform recalibration whenever at least one sensor is replaced;

to set the maximum duration indicative of a jam or an obstruction in the duct conveying the substance whose relative humidity or water activity is being measured; more precisely, if relative humidity or water activity varies only over very narrow limits during said maximum duration, it is then deduced that measurements are continuing to be performed on the same fraction of the substance, and that consequently the duct is probably obstructed, with an appropriate message being placed on the screen 504; and to determine whether or not a printer is present for producing hard copy of the results.

The second subprogram serves to perform the measurements per se. It may comprise three blocks, for example:

a block for measuring temperature and water activity;
a block for controlling the keyboard 502; and
a block for controlling the RS232C interface 508.

When special events occur, the subprogram branches to the second and third blocks. After execution, control is returned to the first block. The second block monitors so-called "function keys" F1 to F10 on the keyboard 502, giving them the following meanings, for example:

F1: Select the sensor whose measurement values are to be displayed on the screen, by default this is sensor No. 1, it is this selection which controls, in particular, the selector 304 in the central unit 300;

F2: Display in text mode the measurement values from the sensors selected by F1, and more precisely the current date, the current time, the real measurements, the reference values, the minimum and maximum values, the alarm values, and possibly also error messages or warning messages (in particular when an alarm value is exceeded or a measurement window is exited);

F3: Displaying graphics, and in particular a first graph of water activity as a function of time and a second graph of temperature as a function of time; it is also possible to display reference values, minima and maxima, measurement means and the most recent measured values; the measurement window is delimited by horizontal first and second straight lines and the reference value by a third horizontal straight line situated between the first two; if an error or the like appears in a measurement from another sensor, a message is displayed; this ensures that all of the sensors are monitored simultaneously;

F4: Displaying graphics analogous to that obtained with key F3, together with an additional display of water content as a function of time, as determined by the water activity and temperature information and by using the stored isotherms corresponding to the substance on which measurements are being performed;

F5: A different form of display in which the water content and/or water activity curves, the reference values, the minima and maxima, and the alarm values for each physical magnitude are displayed together with the means and the most recently measured values;

F6: Reinitializing the calculation of means;

F7: A summary of the measurements from all four sensors simultaneously, together with their respective identifiers;

F8: Displaying the N most recent warning or error messages for each of the sensors;

F9: Reinitializing the message display, while nevertheless retaining the old messages in memory in association with each measurement; and F10: Stopping the program.

Naturally, the subprograms of keys F4 and F5 cannot be activated unless stored isotherms exist for the selected sensor.

Finally, the third block controls the serial interface 508 using a predetermined protocol. More precisely, as soon as a message appears on this interface from the computer 600, the subprogram of the first block is interrupted to branch to the third block. Depending on the type of message received, the response may be immediate, or else it may be deferred until the subprogram currently running in the first block has terminated (in particular if measurement parameters are modified). These arrangements make it possible, in particular, for the computer 600 to operate as a "master" while the computer 500 operates as a "slave". Naturally, the opposite configuration would also be possible.

The third subprogram to which access is given by the main program is a display of the X most recent measurements, where X may be of the order of several thousand to several tens of thousands, for example. More precisely, the measurement subprogram described above systematically stores the following information in mass memory in the form of an X-item stack:

time and date of measurement;

temperature, relative humidity or water activity, and water content; and errors that appear during such measurement.

The third subprogram enables a given sensor to be selected, a window to be chosen, and the chosen window to be applied to the X most recently stored measurements, to extract therefrom those measurements which lie within the window, in particular for display purposes and/or for creating a special file on a floppy disk or a hard disk.

The fourth subprogram accessible from the main program is intended to enable a sensor to be recalibrated. In particular, if one of the sensors appears to be giving incorrect or incoherent measurements, use is made of a standard solution of a non-saturated salt whose relative humidity behavior as a function of temperature is known accurately. The sensor is placed in such a manner as to come into contact with the solution and the subprogram then takes up a stage during which it waits for pressures to stabilize. Once stabilization is achieved, recalibration is performed by comparing the values provided by the sensor with the known expected values.

Finally, the fifth subprogram is a user help program and is suitable for being called up at any time.

The sensor and the installation of the present invention have the following advantages:

the measurements of temperature and of relative humidity or water activity are extremely accurate (temperature: $\pm 0.05°$ C., relative humidity: $\pm 0.10\%$); for relative humidity, this high level of accuracy is due in particular to the fact that the measurement specific to the present invention is in fact a direct measurement of a change in mass without making use of electrical parameters as is the case in the prior art; and response times are short (under static conditions, i.e. without any air flow: about 2 minutes; under dynamic conditions, i.e. with a flow of air: about 12 seconds); these short response times are obtained in particular by using a very thin layer of adsorbant material on the crystals that sense water activity.

The present invention is advantageously applied to measuring relative humidity, water activity, and water content in all sorts of solid substances, e.g. in granular or powder form.

Particular examples include:

agricultural substances and food products such as fertilizers, cereals, forage, spices, tobacco, pet food, dry foods, biscuit manufacturing, powdered milk and egg, potato flakes;

dry pharmaceutical products such as powders or tablets;

inorganic chemical products;

building materials such as plaster or cement; and plastics.

Measurements may also be performed in association with dryers or mixers for all sorts of substances.

Naturally the present invention is not limited to the embodiment described above and shown in the drawings, and the person skilled in the art will be able to make variations or modifications within the scope of the invention.

I claim:

1. A relative humidity or water activity sensor comprising, in combination:

a body defining a cavity;

at least one membrane suitable for passing water vapor while constituting a barrier to liquids, the membrane being situated between the cavity and the medium whose relative humidity and/or water activity is to be measured;

at least two humidity sensing elements disposed at substantially equal distances from the membrane, each of said at least two humidity sensing elements being a resonant humidity sensing element comprising a crystal plate coated at least in part with an adsorbent material and disposed inside the cavity;

at least one resonant temperature sensing element also disposed inside the cavity, and means for determining the resonant frequencies of the sensing elements and for deducing the value of the relative humidity or of the water activity of the medium, and also for deducing temperature.

2. A sensor according to claim 1, wherein each of said resonant humidity sensing elements is housed in an open ceramics package.

3. A sensor according to claim 1, wherein the or each of said at least one resonant temperature sensing element is a quartz crystal resonator, and wherein means are provided for determining the resonant frequency of the crystal resonators and for deducing the temperature value therefrom.

4. A sensor according to claim 1, wherein two temperature sensing elements are provided, one of which is situated at substantially the same distance from the membrane as the humidity sensing element(s) and the other of which is situated further from the membrane, and wherein temperature regulation means are provided including heater means disposed inside the cavity and controlled as a function of the difference between the temperatures measured by the two temperature sensing elements.

5. A sensor according to claim 4, including two identical humidity sensing elements disposed at substantially equal distances from the membrane and further including a first printed circuit carrying both humidity sensing elements and the first temperature sensing element, and a second printed circuit carrying the second temperature sensing element and the heater means, the first printed circuit being disposed between the second printed circuit and the membrane(s).

6. A sensor according to claim 5, further including a removable connector whose connection elements fixed to the sensor also constitute means for assembling the two printed circuits one above the other.

7. A sensor according to claim 1, wherein a stainless steel first membrane is provided in which a plurality of small-sized holes are formed, and wherein an expanded polytetrafluoroethylene second membrane is provided, with the two membranes being placed substantially one against the other and with the stainless steel membrane being situated on the outside relative to the cavity.

8. A sensor according to claim 7, wherein the two membranes are mounted on a support ring itself removably mounted on the body of the sensor.

9. A sensor according to claim 7, wherein: the thickness of the steel membrane lies in the range 0.02 mm to 0.05 mm; the diameter of the holes lies in the range 0.02 mm to 0.08 mm; and the area of the holes represents about 15% to about 25% of the total area of the membrane.

10. An installation for measuring water activity and water content of one or more substances in various locations of industrial processing equipment, the installation comprising:
- a plurality of sensors according to claim 1;
- optical modulator means associated with each sensor for delivering an optical signal representative of the electrical resonance signal of the humidity sensing element(s) of the associated sensor; and
- a central unit connected to the optical modulator means by a plurality of optical fibers and itself comprising:
- a plurality of optical demodulators each associated with a respective one of the sensors and suitable for converting received optical signals into electrical signals;
- selector means for applying a selected one of said electrical signals on an output;
- frequency measurement means; and
- means for controlling the selector means and for converting frequency values into relative humidity or water activity values for each of the sensors.

11. An installation according to claim 10, wherein each sensor includes at least two quartz crystal sensing elements, and in that the optical modulator means further include selector means for modulating a selected one of the electrical resonance signals of the various sensing elements.

12. An installation according to claim 11, wherein each sensor includes at least one humidity sensing element and at least one temperature sensing element, and wherein the selection and control means further include means for calculating water content values for the substance(s) on the basis of the water activity values and the temperature values obtained and on the basis of stored water activity/water content isotherm curves associated with the substance(s) whose water activity is being measured.

13. An installation according to claim 10, further including display means for displaying changes in water activity and/or water content of the substance(s) as a function of time.

14. An installation according to claim 10, further including means for comparing the water activity or water content values with at least one threshold value and for indicating when the threshold(s) is/are exceeded.

* * * * *